US010669520B2

(12) United States Patent
Ho et al.

(10) Patent No.: US 10,669,520 B2
(45) Date of Patent: Jun. 2, 2020

(54) AUTOMATED BIOREACTOR SAMPLING AND GLUCOSE MONITORING SYSTEM

(71) Applicants: Timothy Ray Ho, Atlanta, GA (US); Lewis Ho, Lawrenceville, GA (US)

(72) Inventors: Timothy Ray Ho, Atlanta, GA (US); Lewis Ho, Lawrenceville, GA (US)

( * ) Notice: Subject to any disclaimer, the term of this patent is extended or adjusted under 35 U.S.C. 154(b) by 237 days.

(21) Appl. No.: 15/957,908

(22) Filed: Apr. 20, 2018

(65) Prior Publication Data
US 2018/0362916 A1    Dec. 20, 2018

Related U.S. Application Data

(60) Provisional application No. 62/520,039, filed on Jun. 15, 2017.

(51) Int. Cl.
*C12M 1/36* (2006.01)
*C12M 1/34* (2006.01)
*C12M 3/00* (2006.01)
*C12M 1/12* (2006.01)
*C12M 1/00* (2006.01)

(52) U.S. Cl.
CPC ............ *C12M 41/48* (2013.01); *C12M 23/04* (2013.01); *C12M 23/48* (2013.01); *C12M 29/00* (2013.01); *C12M 29/14* (2013.01); *C12M 41/12* (2013.01); *C12M 41/32* (2013.01)

(58) Field of Classification Search
None
See application file for complete search history.

(56) References Cited

U.S. PATENT DOCUMENTS

| | | | |
|---|---|---|---|
| 4,307,620 A | 12/1981 | Jiskoot | |
| 4,942,770 A | 7/1990 | Seifert et al. | |
| 5,409,841 A | 4/1995 | Chow | |
| 5,998,184 A * | 12/1999 | Shi | C12M 23/08 435/176 |
| 7,213,474 B2 | 5/2007 | Bjork et al. | |
| 7,848,848 B2 | 12/2010 | Busacca et al. | |
| 8,281,672 B2 | 10/2012 | Lee et al. | |
| 9,986,942 B2 * | 6/2018 | Brauker | A61B 5/14532 |
| 2005/0158701 A1 * | 7/2005 | West | C12M 41/48 435/3 |
| 2007/0122829 A1 * | 5/2007 | Ballerstadt | G01N 33/543 435/6.16 |
| 2018/0298343 A1 * | 10/2018 | Sivakumaran | C12N 5/0686 |

FOREIGN PATENT DOCUMENTS

EP    1 508791    8/2003

* cited by examiner

*Primary Examiner* — Nina Bhat

(57) ABSTRACT

Disclosed herein is an improved automatic sampling and biochemical monitoring system for a microbial or cell culture or a biochemical reaction in a bioreactor.

15 Claims, 9 Drawing Sheets

(A)

(B)

AUTOMATED BIOREACTOR SAMPLING AND GLUCOSE MONITORING SYSTEM

This application claims the benefit of U.S. provisional application No. 62/520,039, entitled An Automated Bioreactor Sampling and glucose monitoring System, filed on Jun. 15, 2017.

FIELD OF THE INVENTION

The present invention relates to an apparatus for automatic sampling of the liquid sample from a bioreactor for microbial or cell culture and to also automatically measure the glucose concentration of the collected sample.

BACKGROUND

Apparatuses designed for cultivation of microbial organisms or eukaryotic cells, known as bioreactors or fermentors, have been used for production of various biological or chemical products in the pharmaceutical, biotechnological and beverage industry. A typical bioreactor includes a vessel containing culture medium in a sterile environment that provides the various nutrients required to support growth and production of the homogeneous biological agents of interest. Effective cell culture process requires appropriate supplies of nutrient substances, such as glutamine, glucose, and other medium components; and gas, such as oxygen and carbon dioxide, for growing cells in a bioreactor. In addition, timely control of physiological conditions, such as appropriate pH, temperature, and osmolality is required for mass production of microbial and cell cultures. To conduct all of these control schemes the analysis of these bioprocessing parameters is required and performed by in-situ sensor or on-line/off-line sampling and analysis. Imperative utilization of biosensors has acquired paramount importance in the field of not only bioprocessing but also in food safety standards, defense, security, and environmental monitoring. This has led to an exponential growth of related R&D efforts around the world in recent years. However, on-line/off-line analysis remains the most popular and practical approach for bioprocessing because of the wide availability of off-line analytical instruments. During a microbial or cell culture process, therefore, aseptic withdrawal of a culture broth sample that is representative of the overall microbial or cell culture condition is critical for monitoring the performance of the cell culture or fermentation process and for controlling the process or troubleshooting of any process problems. Conventional sample withdrawal from a bioreactor, fermentor, or medium holding vessel, however, is typically performed by a series of manual operations, including purging of the sampling line, connecting a sample device aseptically to the line, removing the sample from the bioreactor, and closing the line. The purge step is usually required at the beginning of each sampling step to push the residual sample in the sampling line from the previous sampling into a waste reservoir. The conventional sample withdrawal procedure results in the waste of the sample held in the main sampling line, and requires an additional step to switch the sampling line between the waste reservoir and the actual sample container. Most patents including U.S. Pat. Nos. 8,281,672, 7,848,848, 7,213,474, 4,942,770, 5,525,301, etc. taught the use of various automated aseptic sampling devices for bioreactors. All of them have the sampling uptake point inside the vessel in a stationary position. Therefore, it would always have the sample remain in the entire or partial portion of the line depending on the configuration of devices and sampling procedures after a given amount of sample has been collected. The remaining sample requires to be flushed or purged to the waste for the next segment of fresh sampling. This innovation develops a sampling device not only to collect the sample aseptically in any quantity of interest, but to also not require flushing the residual sample to the waste.

As mentioned, glucose is the most important carbon source for a cell or microbial culture. It is therefore the key component of the culture medium most commonly used as an indicator for controlling the culture. Glucose concentration of microbial or cell culture is most commonly measured off-line by an enzymatic glucose analyzer or a glucose analyzer of which the measurement includes glucose and many other biochemicals in the culture medium such as pH, Lac, Gln, $MH_4$, $PO_2$, $PCO_2$, Na+, K+, $PO_4$, Gly, Ca++. Most of these analyzers and consumables are expensive, particularly, when it is configured for automatic measurement. Lately, the use of a manual inexpensive blood glucose meter for glucose measurement in microbial and cell cultures has gained popularity because of its low cost, small sample volume required and fast response time. However, it is manually operated and requires to be calibrated because its accuracy is medium-dependent on each medium used in the cultures.

This disclosure provides a risk-free and accurate sampling method to automatically collect the fluid sample from a bioreactor in an exact amount as low as <1 ml, no waste of any fluid, and no requirement of purging or flushing. It is also coupled with a low cost automatic glucose monitoring system to measure the glucose concentration of the collected sample automatically, accurately and economically.

SUMMARY

In one aspect, disclosed here is an automatic sampling and glucose monitoring system wherein the system comprises:

Sampling assembly 1 which further comprises a) a holding assembly 20 secured on a standard open port on the head plate 101 or on top of the bioreactor vessel 100 and able to steadily hold a rigid sampling tube 31 to reach inside of the vessel; b) a connector 10 connecting the rigid sampling tube 31 with a flexible tubing 50 outside of the vessel, wherein the flexible tubing 50 is further connected with a rigid discharging end 51 at the end; c) a positive displacement pump 60 coupled with the flexible tubing 50 to transport the sample fluid from inside of the bioreactor vessel 100 through the sampling tube 31, flexible tubing 50 and discharging end 51 to a designated sample collecting container 70 held in an array tray 401;

A glucose monitoring assembly 202 comprises a handheld blood glucose meter 200 coupled with a test strip 201 for analyzing and displaying the glucose concentration of the sample fluid;

A positioning assembly 300A coupled with the sampling assembly 1 and the glucose monitoring assembly 202 comprising a X-Y-Z position table or a X-Y position table 300 equipped with a linear actuator and a motor 306 for positioning along the Z-axis wherein the table is coupled with the glucose monitoring assembly 202 and sampling assembly 1 to position the discharging end 51 of the sampling assembly 1 and the meter 200 of the glucose monitoring assembly 202 on the table 300;

A control apparatus connected by wire or wirelessly to the sampling assembly 1, glucose monitoring assembly 202 and positioning assembly 300A wherein the control apparatus is configured and programmed to coordinate the positioning of the discharging end 51 for delivering the sample fluid to the designated sample collecting container 70, of the meter 200 to engage it with a designated test strip 201, then to contact the test tip to the sample fluid of the designated sample collecting container 70 and to further suck up the sample fluid by capillary action to the meter 200 for analysis, and to finally disengage the strip 201 from the meter 200 to the waste collector 403, wherein the apparatus is also configured to control the temperature of a cabinet comprising the discharging end 51, the sample collecting container 70, the glucose monitoring assembly 202, the positioning assembly 300A and the control apparatus.

In another aspect the sampling assembly 1 wherein the rigid sampling tube 31 held in the holding assembly 20 is fixed and sealed in the assembly and the tip of the sampling tube 31 is always submerged below the liquid level of the bioreactor vessel 100; wherein the flexible tubing 50 connected to the sampling tube 31 is branched off before the rigid discharging end 51 with another flexible tubing 50 equipped with a check valve 52 followed with an air filter 63 in the end; wherein a pinch valve 62 is applied on the main flexible tubing 50 before the discharging end 51 and another pinch valve 61 is applied on the branched tubing 50A before the air filter 63; wherein positive displacement pump 60 is bi-directional.

In another aspect the sampling assembly 1 wherein the rigid sampling tube 31 held in the holding assembly 20 is movable, wherein the assembly comprises a solid body extended to inside of the bioreactor vessel 100 with a narrow opening in the center to accommodate the rigid movable sampling tube 31 to slide steadily and freely up and down inside of the bioreactor vessel 100; wherein the connector is movable and one end of the connector is connected with a movable rigid sampling tube 31 and the other end with a flexible tubing 50 equipped with a check valve 52 and ended with a rigid discharging end 51, wherein the movable connector 10 is further connected with the holding assembly 20 using a retractable tube 30; wherein the movable connector 10 is further coupled and driven with a driving assembly 40, wherein the driving assembly 40 comprises a linear actuator and a motor secured in a fixed position by a supporting frame or holder secured on or around the bioreactor vessel 100 and moves the movable connector 10 along with the sampling tube 31 up and down through the center opening of the holding assembly 20.

In one aspect, disclosed here is an automatic sampling and glucose monitoring system for a bioreactor wherein the system can be used alone by removing the glucose monitoring assembly 202 as an automatic sampling system for a bioreactor to collect samples automatically for further analysis using other analytical instrument; wherein the system can also be used alone by removing the sampling assembly 1 as an automatic glucose measurement system for measuring the glucose concentration of the collected samples held in an array tray 401.

DESCRIPTION OF THE EMBODIMENT

Figure 1:
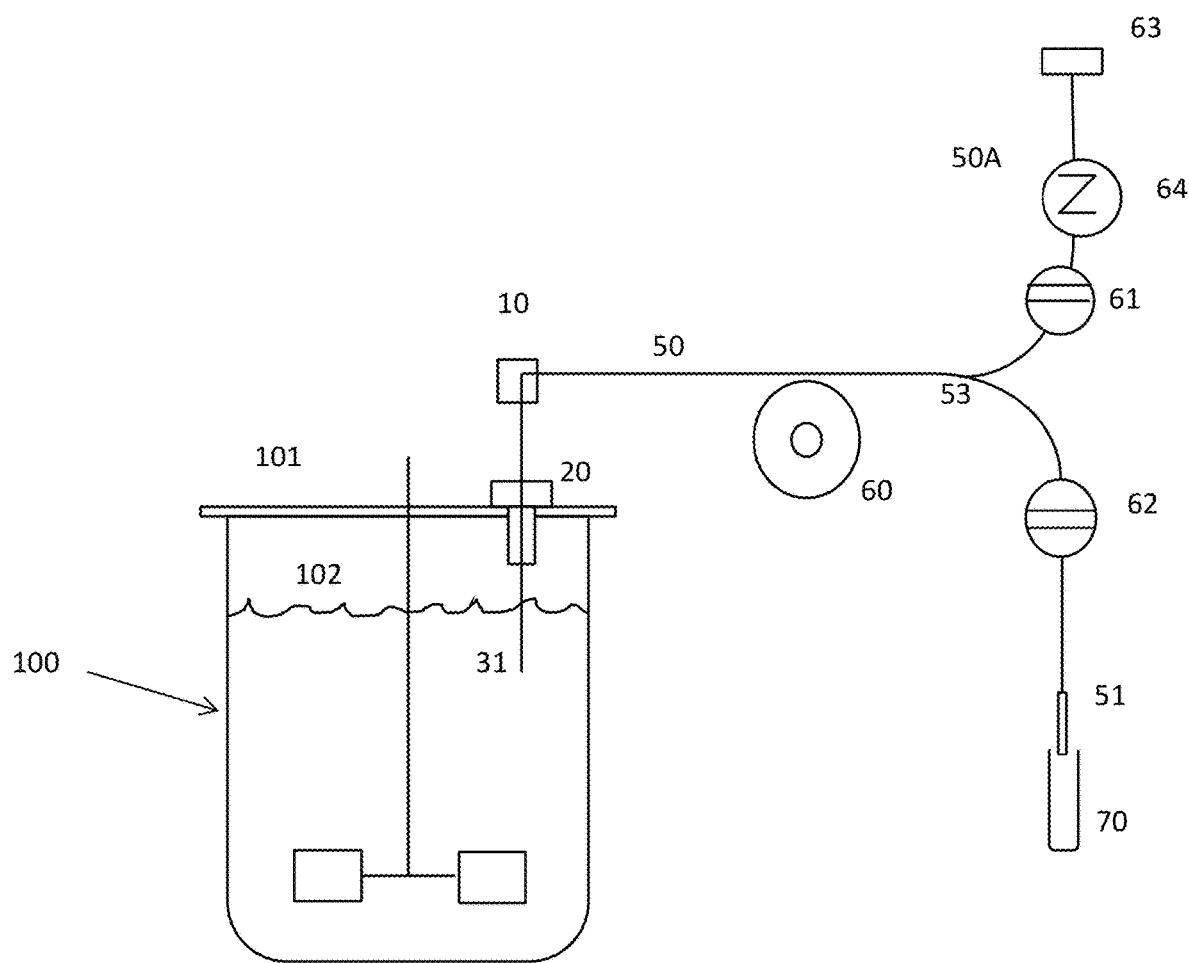
FIG. 1 shows the schematic diagram of the automatic sampling system with a fixed sampling assembly according to the present disclosure.

In the following detailed description, reference is made to the accompanying drawings that form a part here of, and in which are shown by way of illustration several specific embodiments of apparatus, systems, and methods. It is to be understood that other embodiments are contemplated and may be made without departing from the scope or spirit of the present disclosure. The following detailed description, therefore, is not to be taken in a limiting sense.

The embodiment as described here is an automated bioreactor sampling and glucose monitoring system comprising:

A) A sampling assembly comprising:
   a) a holding assembly secured on a standard opening port on the head plate or on top of a bioreactor vessel and managed to steadily hold a rigid sampling tube to reach inside of the vessel;
   b) a connector connecting the rigid sampling tube and a flexible tubing outside of the vessel, wherein the flexible tubing is further connected with a rigid discharging end;
   c) a positive displacement pump coupled with the flexible tubing to transport the sample fluid from inside of the bioreactor vessel through the sampling tube, flexible tubing and discharging end to a designated sample collecting container;

B) A glucose monitoring assembly comprising:
   a sampling mechanism coupled with an glucose analyzer to analyze and record the data of the glucose concentration of the sample fluid;

C) A tray assembly comprising an array tray configured to hold the at least one sample collecting container and a test strip of the glucose monitoring assembly wherein the glucose monitoring assembly comprises an on-site handheld glucose meter;

D) A positioning assembly coupled with the sampling assembly and the glucose monitoring assembly comprising
a X-Y-Z position table or a X-Y position table equipped with a linear actuator and a motor for positioning along the Z-axis wherein the table is coupled with the glucose monitoring assembly and the sampling assembly to position the discharging end of the sampling assembly and the analyzer or the sampler of the glucose monitoring assembly on the table; and E) A control apparatus connected by wire or wirelessly to the sampling assembly, glucose monitoring assembly and positioning assembly wherein the control apparatus is configured and programmed to coordinate the positioning of the discharging end for delivering the sample fluid to the designated sample collecting container, the positioning of the glucose monitoring assembly to sampling the specified sample for the analyzer to analyze and process, wherein the apparatus is also configured to control the temperature of a cabinet comprising the discharging end, the array tray, the glucose monitoring assembly, the positioning assembly and the control apparatus.

As disclosed herein is an automatic bioreactor sampling and glucose monitoring system comprising a sampling assembly, a glucose monitoring assembly, a positioning assembly, a control apparatus and an enclosed cabinet for sampling from a bioreactor vessel not limited to 2, 3, 4, 5, 6, 7, 8, 9, and 10.

As disclosed herein the sampling assembly comprises a holding assembly wherein the assembly is screwed on a standard opening port commonly the size of 12 mm ID (inner diameter) or the like on the top or head plate of the vessel and configured to hold steadily a rigid sampling tube reaching inside of the vessel to collect the liquid sample. The rigid sampling tube can be held in two ways: (1) the rigid sampling tube held in the holding assembly is fixed, stationary and sealed in the assembly and the tip of the sampling tube is always submerged below the liquid level of the bioreactor vessel for sampling; (2) the rigid sampling tube held in the holding assembly is movable, wherein the assembly comprises a solid body extended to inside of the bioreactor vessel with a narrow opening in the center to accommodate the rigid movable sampling tube to slide freely and steadily up and down inside of the bioreactor vessel. In order to collect the exact quantity of sample aseptically from the vessel without any waste or leaving any residual sample in the sampling line, both methods described above are different in using the sampling assembly and sampling procedure.

For using the fixed sampling tube, a flexible tubing connected to the rigid sampling tube is branched off before the rigid discharging end with another flexible tubing equipped with a check valve followed with an air filter at the end, wherein a pinch valve is applied on the main flexible tubing before the discharging end and another pinch valve is applied on the branched tubing before the air filter.

In FIG. 1 is illustrated a schematic diagram of an automatic sampling system with a fixed rigid sampling tube to sample the fluid sample from the bioreactor vessel 100. The sampling tube 31 is sealed and fixed on the holding assembly 20 on a head plate 101 of the vessel and is always submerged below liquid level 102. After the discharging end 51 is positioned on the collecting container 70, the pinch valve 62 is opened while the other pinch valve 61 is closed, the peristaltic pump 60 is activated to pump forward, and a given amount of the sample fluid is pumped out from the vessel 100 by a given pumping time moving through the flexible tubing 50 and entering the container 70. After the pump is stopped and the pinch valve 62 is closed and valve 61 is opened. The check valve 64 on the tubing 50A is used to prevent the sample fluid from flowing toward the sterile air filter 63. The pump 60 is reactivated in the reverse direction and the sample fluid remaining in the tubing 50 flows back to the vessel 100. The pump 60 is then stopped and the pinch valve 61 is closed and pinch valve 62 re-opened. The pump 60 is reactivated to pump forward to purge out the small amount of remaining sample fluid between Y-connector 53 and discharging end 51 to the collecting container 70. At this point, there is small amount of sample fluid that is pumped up to the tubing 50 again. The pinch valve 61 is re-opened and valve 62 is closed. The pump 60 is reactivated backwards or in reverse to flush out the last remaining fluid sample back to the vessel 100, and the pinch valve 61 is closed for the next sampling cycle. As noted, the pump 60 is bi-directional and the connector 10 is fixed with the rigid sampling tube 31. The entire sampling process is under aseptic condition and there is no waste sample. The entire sampling tubing is clear after sampling and ready for the next sampling. The integrity of the entire process is intact. The advantage of this sampling device and method is simple and requires no moving parts of the sampling assembly contacting the sample fluid. But it is required to flush a portion of the sampled fluid back to the vessel to clear the line aseptically.

For using the movable rigid sampling tube, the movable connector connects with the rigid sampling tube in one end and the flexible tubing equipped with a check valve and a discharging end in the other end; wherein the movable connector is further connected with the holding assembly using a retractable tube; wherein the movable connector is further coupled and driven with a driving assembly, wherein the driving assembly comprises a linear actuator and a motor secured in a fixed position by a supporting frame or holder secured on or around the bioreactor vessel and moves the movable connector along with the sampling tube up and down through the center opening of the holding assembly. As noted, the rigid sampling tube is enclosed inside of the retractable tube and forms a closed system. As the movable connector is driven downward by a driving assembly, the retractable tube is compressed and the rigid sampling tube moves downward and submerges below the liquid level of the bioreactor vessel. Likewise, as the movable connector is driven upward by the driving assembly, the retractable tube is expanded and the rigid sampling tube moves upward and emerges above the liquid level of the bioreactor vessel. The rigid sampling tube remains inside a closed system and integrity of the system is intact.

A linear actuator driven by a motor or the like secured in a fixed position by a supporting frame or a holder on or around the bioreactor vessel 100 and is connected with the movable connector to move up and down along with the rigid sampling tube through the holding assembly to submerge into or emerge from the fluid of the bioreactor vessel; the motor is a linear motor wherein the electric motor that has had its stator and rotor "unrolled" so that instead of producing a torque (rotation) it produces a linear force along its length. If the motor is a regular electric motor, the linear actuator is a mechanical actuator based on simple rotating screw and nut to create the linear motion.

Figure 2:
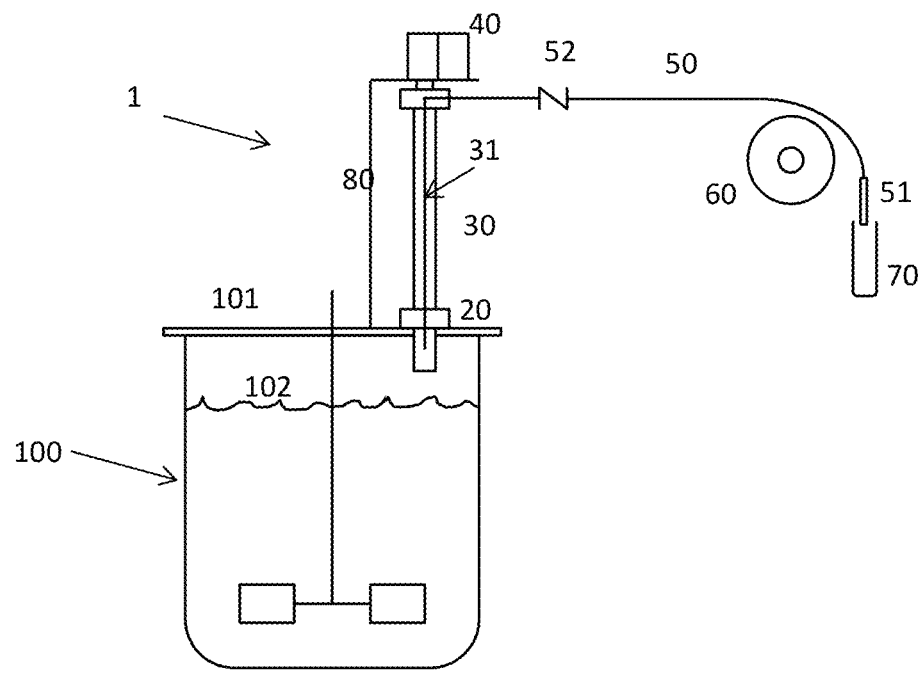
FIG. 2 shows the schematic diagram of the automatic sampling system with a movable sampling assembly according to the present disclosure wherein (A) the sampling tube submerges below the liquid level for sampling and (B) the sampling tube is retracted and moved above the liquid level.
Figure 2:
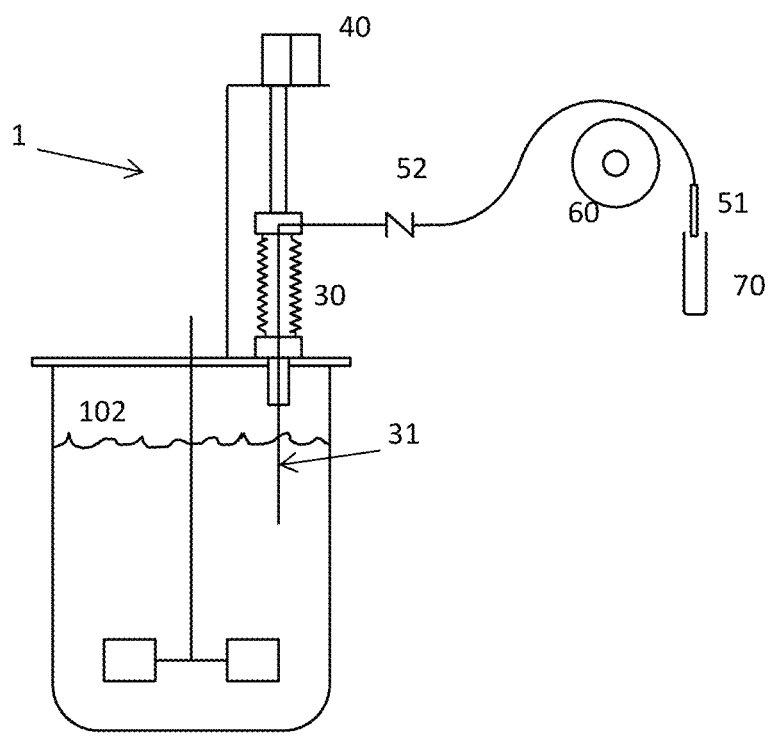

In FIG. 2 is illustrated the schematic diagram of an automatic sampling system with a movable rigid sampling tube to sample the fluid sample from the bioreactor vessel 100 in the following steps (A) the linear actuator 40 secured by a fixed support frame 80 on the head plate 101 of the bioreactor 100 pushes the movable connector 10 along with the sampling tube 31 downward and submerges below the liquid level 102 for sampling. The pump 60 is then activated for a given time to draw a given amount of fluid sample from the vessel 100. And then the pump is stopped and (B) the linear actuator 40 is activated and retracts the movable connector 10 along with the sampling tube 31 upward and off the liquid level 102, then the pump 60 is reactivated and continues to pump the entire remaining fluid sample in the sampling tube 31, flexible tubing 50 and discharging end 51 to the collecting container 70.

By following this sampling procedure the exact quantity of sampled fluid can be taken and always moved forward and never backward. The rigid sampling tube is pulled out from the liquid of the bioreactor vessel 100 and enables the pump to continue to clear the residual without any waste.

Figure 3:
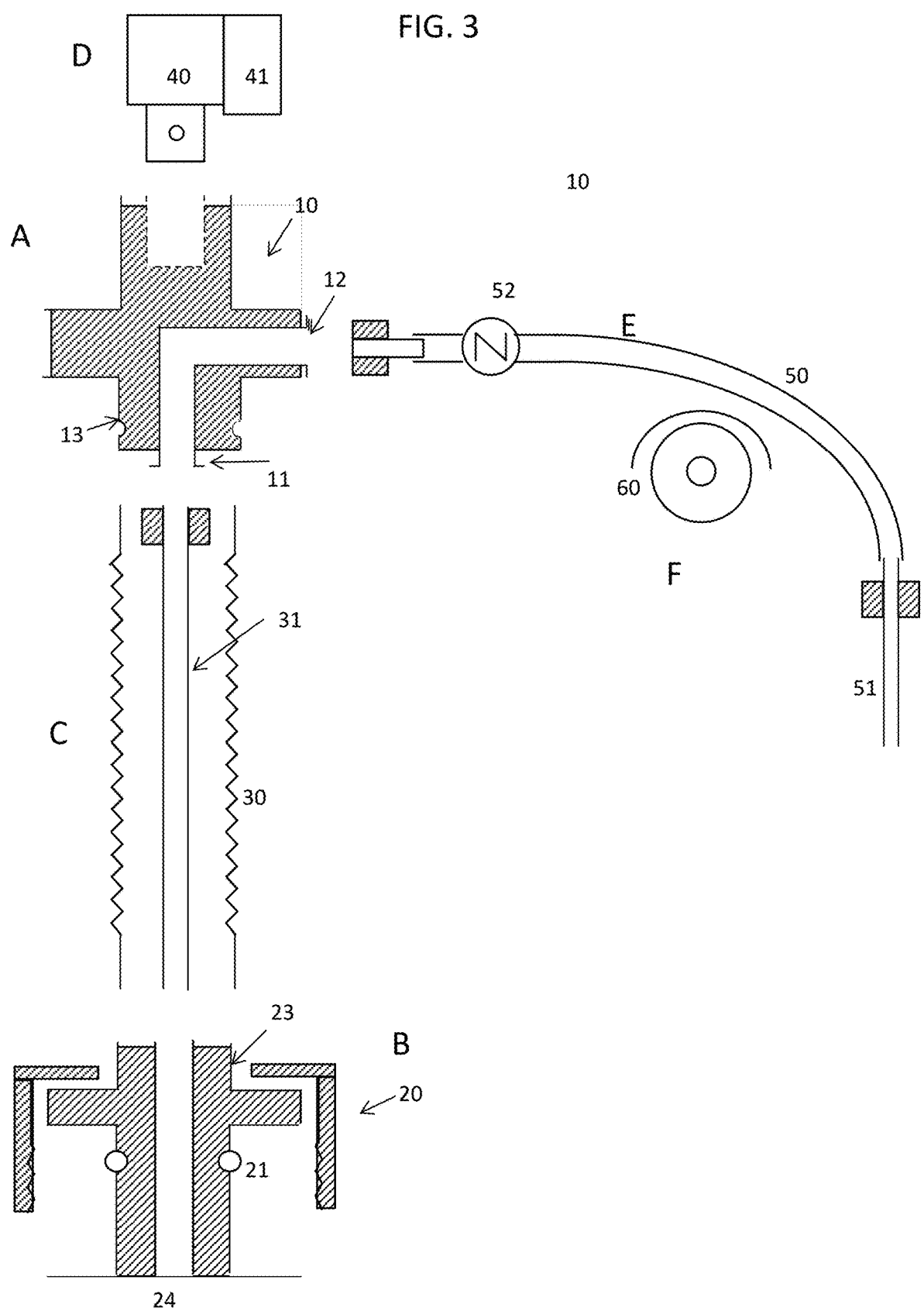
FIG. 3 shows the schematic diagram of the parts of the movable sampling assembly according to the present disclosure including (A) movable connector, (B) holding assembly, (C) retractable tube and sampling tube, (D) linear actuator and motor, (E) flexible tubing and discharging end and (F) positive displacement pump.

In FIG. 3 is further illustrated in detail the components of the sampling assembly 1 with a movable rigid sampling tube including (A) movable connector 10, (B) holding assembly 20, (C) retractable tube 30 and sampling tube 31, (D) linear actuator 40 and motor 41, (E) flexible tubing 50 and discharging end 51 and (F) positive displacement pump 60. The holding assembly 20 with O-rings 21 is inserted into the standard opening port and secured by the open screw cap 22. A linear actuator 40 is connected with the movable connector 10 and driven by the linear actuator 40 and motor 41 to move it up and down through the center 24 of the assembly 20. The opening in the bottom of the movable connector 10 with the Luer lock 11 is connected with the rigid sampling tube 31 which can be needle, tube or pipe depending on the sample size. The other opening in the side with the Luer lock 12 is connected with a flexible tubing 50 equipped with a check valve 52 and ended with a rigid discharging end 51 which can be needle, tube or pipe depending on the sample size; the check valve 52 prevents the fluid inside of the tubing from flowing back to the bioreactor vessel 100. A retractable tube 30 is used to connect one lower end 13 of the connector 10 and another end of the holding assembly 23.

As disclosed herein the sampling assembly wherein all components of the assembly are made of autoclavable reusable materials such as stainless steel, glass, polycarbonate, polypropylene, PTFE resin and polymethylpentene. They can be made of single use materials such as plastic which cannot be autoclaved but only sterilized via gamma irradiation or ethylene oxide sterilization. The sampling assembly can therefore be used in a single use bioreactor as an integrated single use system.

As disclosed herein the sampling assembly comprises a positive displacement pump with a channel but not limited to 2, 3, 4, 5, 6, 7 and 8 wherein each channel of the pump is coupled with the flexible tubing of a bioreactor to transport the fluid sample from inside of the bioreactor through the tubing and the discharging end to each designated collecting container; the positive displacement pump preferably is a peristaltic pump or the like to transport fluids without exposing those fluids to contamination from the exposed pump components. The pump is intended to move the fluid inside of the flexible tubing forward only in one direction.

As disclosed herein the sampling assembly comprises a holding assembly wherein the holding assembly is secured by an open screw cap on each of the bioreactor vessel through one of its standard opening ports on the side or bottom of the vessel and sealed with an O-ring; and a movable connector wherein the movable connector comprises two separate paths, of which one end of the first path is connected with the rigid sampling tube and another end is connected with the flexible tubing ended with a rigid discharging end; and one end of the second path is connected with an air inlet control valve wherein the valve is connected to a sterile air supply and another end is open to the chamber enclosed inside of the retractable tubing. The sterile air is supplied during the sampling process to maintain positive pressure and to form an air lock inside of the chamber of the sampling assembly to block the fluid from getting inside of the chamber. As a result, when the sampling tube is retracted back inside of the holding assembly the sampling tube is separated from the fluid inside of the bioreactor and enables to clear the entire remaining fluid in the sampling tube and the flexible tubing to the collecting container.

Figure 4:
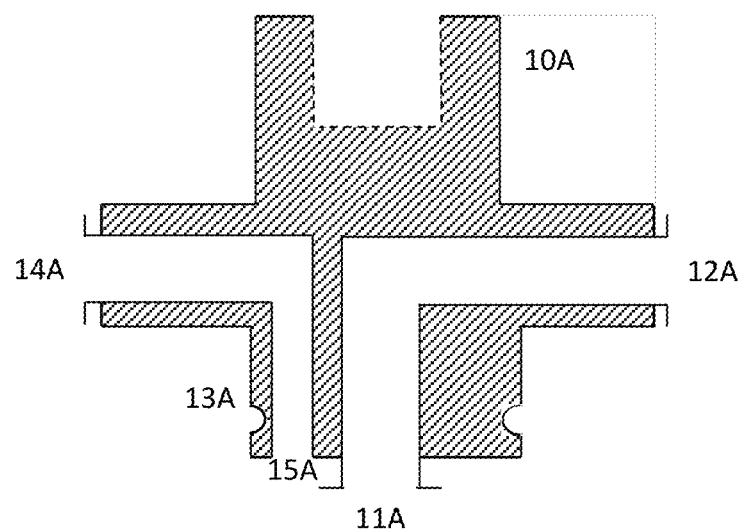
FIG. 4 shows the movable connector of the movable sampling assembly to be used for sampling the sample fluid from the side or bottom of a bioreactor vessel according to the present disclosure.
Figure 5:
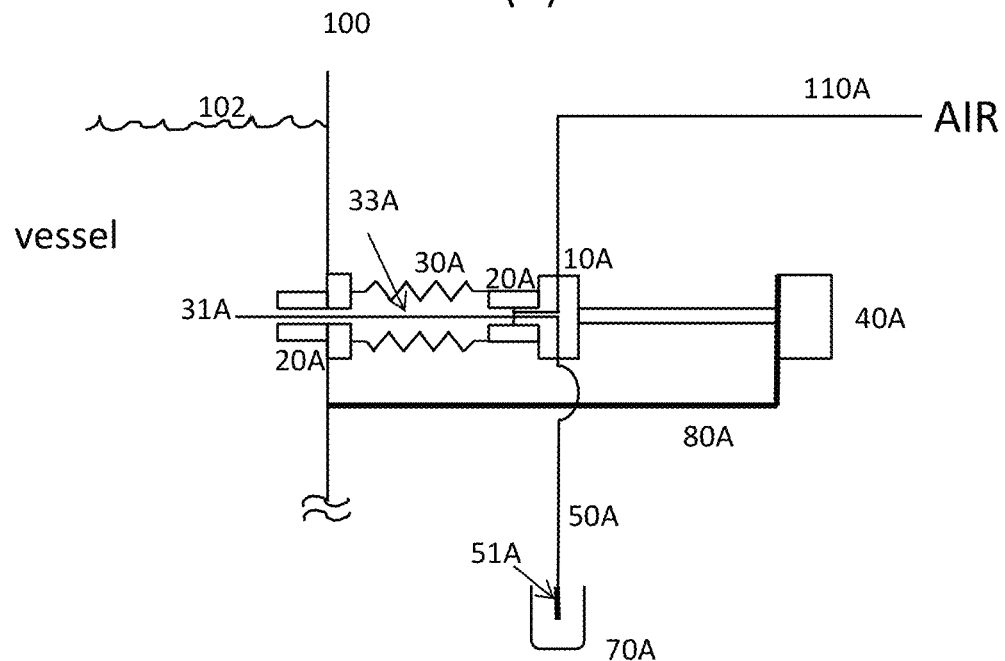
FIG. 5 shows the schematic diagram of the movable sampling assembly on a bioreactor to be used for sampling the sample fluid from the side or bottom of bioreactor vessel as (A) the sampling tube extends out of the holding assembly to reach the fluid and (B) the sampling tube is retracted back to inside of the holding assembly according to the present disclosure.
Figure 5:
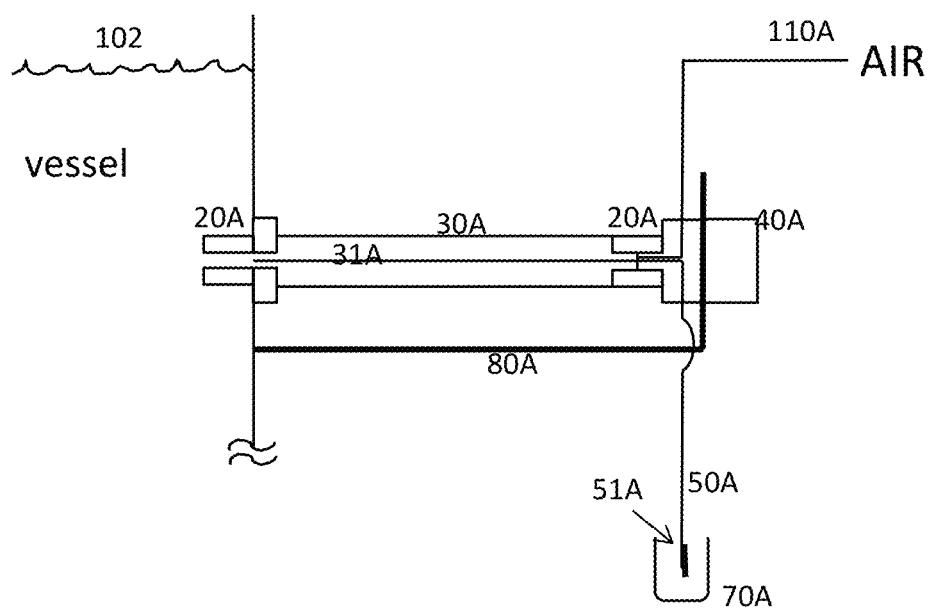

In FIG. 4 is illustrated the movable connector 10A for the sampling assembly to be used for sampling the sample fluid from the side or bottom of vessel 100 as shown in FIG. 5, wherein the connector comprises the connecting ends 11A and 12A for the rigid sampling tube and flexible tubing respectively similar to those shown in FIGS. 1 and 2 and an extra end 14A for connecting to the sterile air supply and the extra corresponding end 15A opening to the chamber 33A enclosed by the retractable tube 30A as shown in FIG. 5.

In FIG. 5 is illustrated the schematic diagram of the sampling assembly on a bioreactor 100 as (A) the linear actuator 40A secured by a fixed support frame or holder 80A on the side of the bioreactor vessel 100 moves the movable connector 10A along with the sampling tube 31A forward and submerges into the fluid of vessel 100 for sampling. At the same time the sterile air supply 110A enters the chamber 33A and forms the airlock inside the chamber 33A. The peristaltic pump is activated for a given time and a given amount of fluid sample is withdrawn from the vessel 100. And then the pump is stopped and (B) the linear actuator 40A is activated and moves the movable connector 10A along with the sampling tube 31A backwards and retracts into the holding assembly 20A and blocks out the fluid of the vessel 100, then the pump is reactivated and continues to pump the entire remaining fluid sample in the sampling tube 31A, flexible tubing 50A and discharging end 51A to the collecting container 70A.

As disclosed herein an array tray configured to hold the at least one sample collecting container wherein the array tray is a tray comprising organizing array to hold each sampling collecting container in designated position and allow the control apparatus to direct the discharging end to discharge and store the sample at the designated position.

As disclosed herein one glucose monitoring assembly comprises a sampling mechanism and a glucose analyzer, wherein the sampling mechanism and a glucose analyzer are an on-site handheld glucose meter and an on-site testing strip, wherein the meter mounted on the table of the positioning assembly is used to analyze the glucose concentration of the sampled culture fluid and transmit the data to the control apparatus and wherein the strip is attached to the meter and served as a sampler to suck the sample from the specified sample collector on an array tray by capillary action, wherein the test strip is also impregnated with enzyme which reacts with the enzyme and analyzed by the meter. The handheld glucose meter is the most popularly used blood glucose meter for monitoring blood glucose concentration for diabetes. It is simple, fast and very inexpensive. If the meter is recalibrated with the culture medium, the glucose concentration of culture medium can be theoretically determined unless some content of the medium severely interferes with the enzymatic reaction. In this disclosure, the glucose meter and strip are integrated as part of the automatic sampling and glucose monitoring system in one cabinet. However this glucose monitoring is only limited to the most commonly used carbohydrate, glucose only. However, most of these instruments are expensive, particularly when it is configured for automatic measurement. The control of glucose concentration is often the most useful control strategy in the bioprocess control of microbial and cell cultures, especially when it can be performed in real time and automatically. There is no affordable automatic on-line glucose measurement instrument available in today's market. In this disclosure the automation of using this very inexpensive and simple handheld glucose meter along with automatic calibration of culture standard medium makes this application possible. The handheld glucose meter is equipped with RS282 or RS485 serial communication protocol to transmit the glucose measurement data to the central computer for processing.

Figure 6:
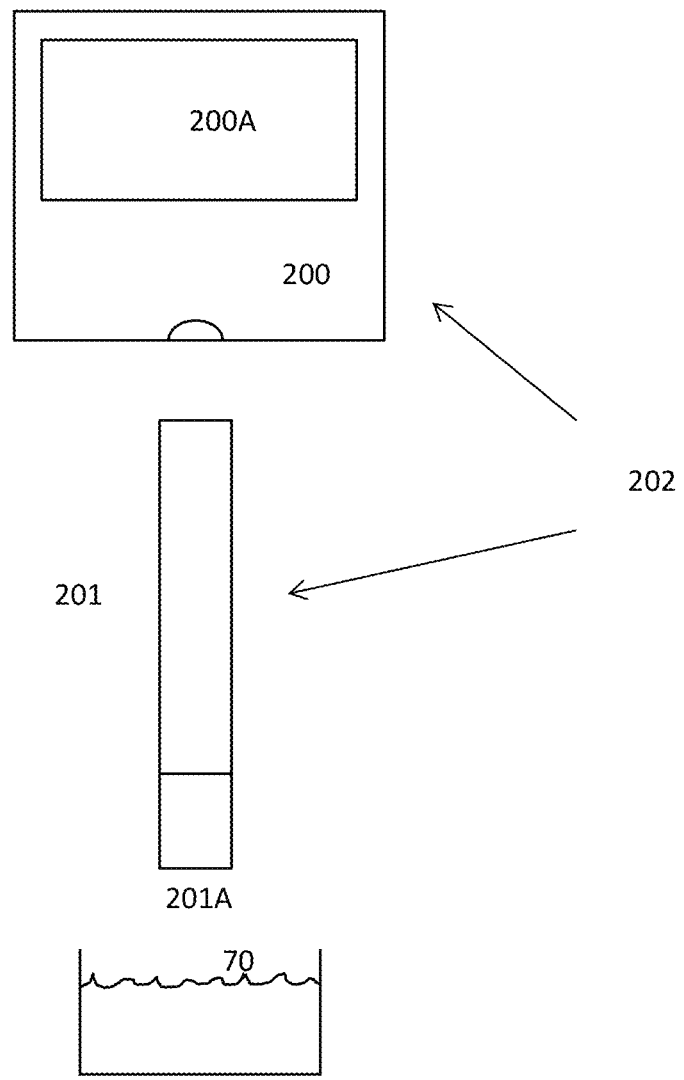
FIG. 6 shows the glucose monitoring assembly comprising a commercial handheld blood glucose meter with signal output and a test strip according to the present disclosure.

In FIG. 6 is illustrated the glucose monitoring assembly 202 comprising a commercial handheld blood glucose meter 200 and a test strip 201. The test strip 201 is first inserted into the slot in the bottom of the meter 200. Then the tip of the test strip 201A engaged in the meter is moved to contact the fluid sample in the collecting container 70 and the sample is sucked into the meter 200 by capillary action for analysis. In 10 seconds or less the measurement is done and the reading of glucose concentration is displayed on the screen 200A and the data is transmitted through RS 232 or RS 485 to the computer for processing.

Currently, most glucose measurement for bioprocessing in today's market uses the same electrochemical method. However, using the same electrochemical and optical technologies has progressed to include more than 10 glucoses in one sample such as pH, pCO2, PO2, Na+, K+, Cl−., Ca++, Gluc and Lac etc. in one glucose analyzer. Nova Bioprofile is one example of these types of devices in the market.

As disclosed herein one glucose monitoring assembly further comprises a sampling mechanism and a glucose analyzer, wherein the sampling mechanism and a glucose analyzer are an on-site sampler and an off-site commercial biochemical analyzer. The on-site sampler is another sampling tube mounted on the table of the positioning assembly connected with a flexible tubing and driven by a peristaltic pump in reverse direction to withdraw the sample from the specified sample collecting container on an array tray and transfer to an off-site glucose or biochemical analyzer described above for analysis.

As disclosed herein one positioning assembly comprises an X-Y-Z position table or a X-Y position table with a linear actuator and motor wherein the position X-Y-Z table provides horizontal and vertical motions for automated machinery such as assembly robots in manufacturing facilities. The table is also known as X-Y-Z stages and slides with motorized linear motion based on bearings which are driven by three drive mechanisms, typically three linear motors or the like; alternatively the position X-Y table provides horizontal motion for automated machinery such as assembly robots in manufacturing facilities. The table is also known as X-Y stages and slides with motorized linear motion based on bearings which are driven by a drive mechanism, typically two linear motors or the like. The X-Y table is mounted vertically with a linear actuator with a linear motor on one horizontal slide to perform the vertical motion in the Z-direction.

As disclosed herein one positioning assembly further comprises a discharging end and a glucose monitoring assembly, wherein the discharging end and a glucose monitoring assembly are secured on the X-Y-Z table or the like of the positioning assembly, wherein the discharging end is positioned to discharge the fluid sample from the bioreactor to the designated collecting container, wherein the glucose monitoring assembly comprising the on-site glucose meter and test strip is positioned to have the meter attaching the test strip on an array tray wherein the test trip is acted as a sampler sampling the fluid sample and delivering and analyzing glucose further by the meter on site, wherein the glucose monitoring assembly comprising the on-site sampler and off-site glucose or biochemical analyzer is positioned to have the sampler sampling and delivering the fluid sample to the off-site glucose or biochemical analyzer for further analyzing and processing.

As disclosed herein one the control apparatus is connected wired or wirelessly with the sampling assembly, glucose monitoring assembly and positioning assembly wherein the control apparatus is configured and programmed to coordinate the positioning of the sampling tube by the linear actuator and motor of the sampling assembly to the vessel fluid for sampling, the activation of the positive replacement pump to pump the sample through the flexible tubing, the positioning of discharging end on the X-Y-Z table or the like for delivering the fluid sample to a designated collecting container, the positioning of the meter to engage with a designated test strip, then to contact its tip to the fluid sample in the designated collecting container held in the array tray while the sample is sucked up via the test strip to the meter by capillary action for analysis and finally to dispose the test strip to a waste collector or the positioning of the sampler to sample and deliver the fluid sample to and communicate with the off-site glucose analyzer for processing the analysis and data communication. The apparatus is also configured to control the temperature of the cabinet where the glucose strips, meter or sampler and the fluid samples are located. The control apparatus may include one or more computing devices capable of processing data; microprocessors, programmable logic arrays, data storage, input devices, output device; human machine interface (HMI) and programmable logic control (PLC) etc.

As disclosed herein one enclosed cabinet comprises a chamber wherein the chamber comprises a discharging end and collecting container of the sampling assembly, the glucose monitoring assembly and the X-Y-Z position table or the like and the temperature of the chamber is controlled; and another chamber wherein the chamber comprises a control apparatus. The enzymatic reaction for the glucose measurement is temperature dependent; a constant temperature is therefore required for all samples and standards to be analyzed inside of the chamber. The chamber is enclosed and controlled at a constant temperature by a heating and cooling mechanism with a temperature controller for the best temperature condition for storage and analysis of samples. The heating mechanism can be hot air or water or the like and cooling mechanism can be superconductive refrigeration or cooling water or the like.

Figure 7:
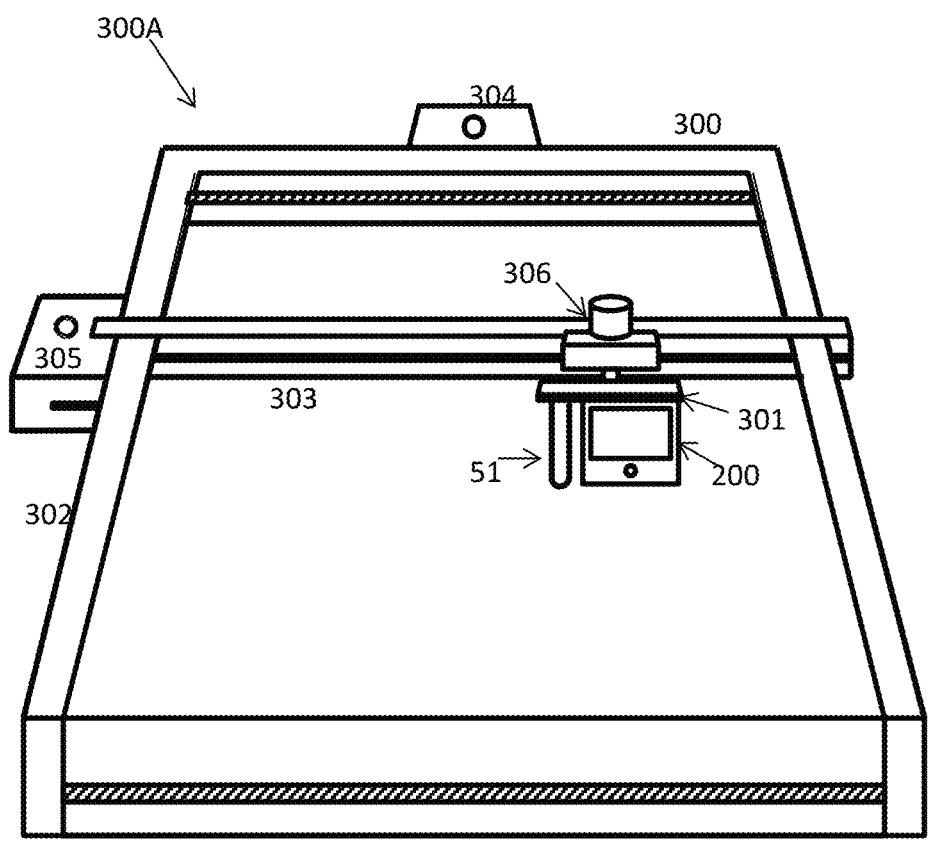
FIG. 7 shows one positioning assembly according to the present disclosure comprising a discharging end from the sampling assembly, glucose meter from the glucose monitoring assembly, and an X-Y-Z position table.

In FIG. 7 is illustrated one positioning assembly comprising one discharging end 51 from the sampling assembly, glucose meter 200 from the glucose monitoring assembly, and one X-Y position table 300 wherein the glucose meter 200 and the discharging end 51 are mounted in a holder 301 and connected to the electric linear actuator/motor 306 to perform the Z-vertical motion. The table is also known as X-Y stages 300 and slides 302, 303 with motorizes linear motions based on bearings which are driven by two drive mechanisms, typically two linear motors 304 and 305. For the system with an off-site glucose or biochemical analyzer, the positioning assembly is mounted with a separate sampling tube to serve as a sampler in replacing the glucose meter shown in FIG. 7.

Figure 8:
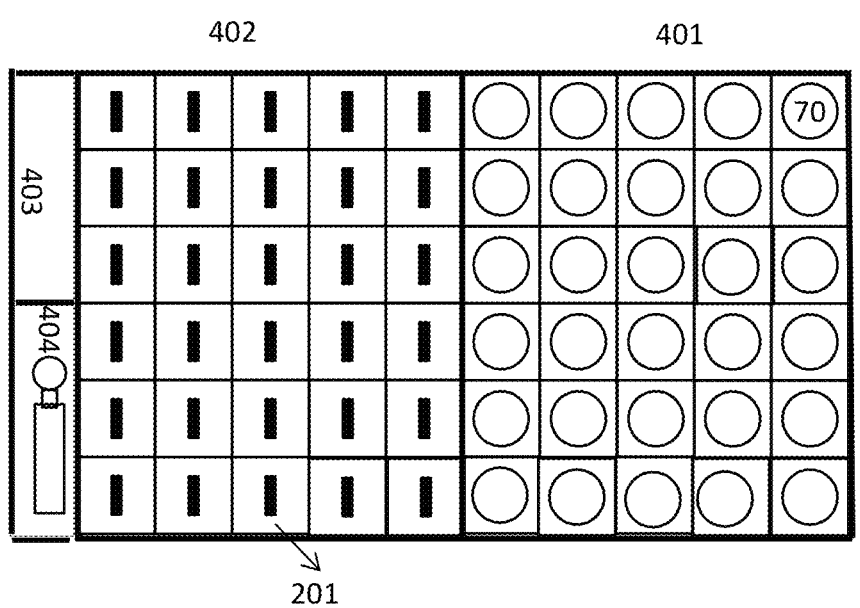
FIG. 8 shows a layout example of an array tray of collecting tubes, a set of test strips and a waste collector of test trips inside of the cabinet according to the present disclosure.
Figure 9:
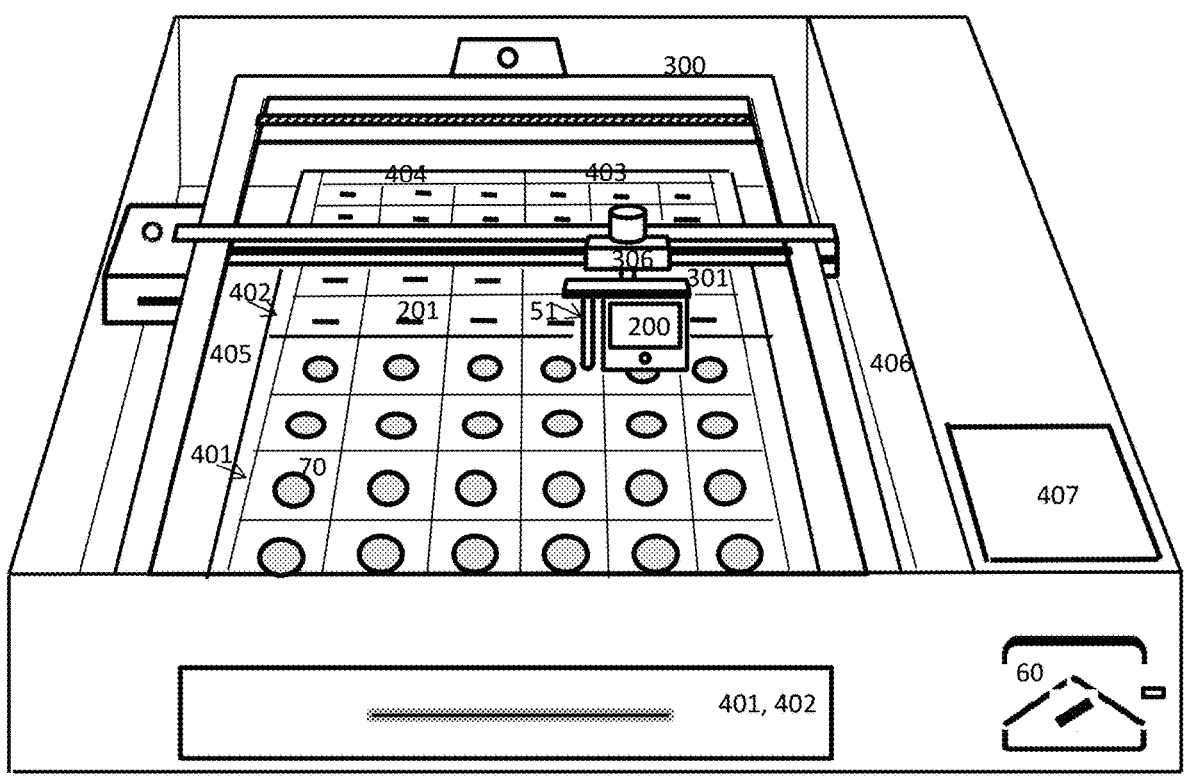
FIG. 9 shows one enclosed cabinet according to the present disclosure comprising a chamber that houses a discharging end and a set of collecting tubes held in an array tray, a glucose meter, a set of test strips and an X-Y-Z position table and another chamber that houses a control apparatus.

In FIG. 8 is illustrated a layout example of an array tray 401 of collecting containers 70, an array tray 402 of test strips 201 and a waste collector of test strips 403 inside of the cabinet 400 as shown in FIG. 9 for the system with on-site glucose meter and test strip. The discharge tube 51 is positioned to receive the sample fluid in the collecting container 70. Then the meter 200 is moved to engage a test strip 201 at a designated position. The meter then moves back to the same collecting container 70 held in the array tray 401 and lowers the tip of strip 201 to the sample fluid. In 10 seconds the reading of glucose concentration is displayed and transmitted through RS282 or 485 to the computer for processing. In the meantime, the meter 200 is moved to the waste collector 403 position to disengage the strip and return to the original position 404. For the system with an off-site glucose or biochemical analyzer the array tray 401 comprises only the sample collecting containers 70.

In FIG. 9 is illustrated one enclosed cabinet 400 for the system with on-site glucose meter and test strip comprising two chambers 405 and 406 wherein the chamber 405 comprises one discharging end 51 and a set of collecting containers 70, one glucose meter 200, a set of test strips and one X-Y-Z position table 300 and wherein the temperature of the chamber 405 is controlled; and wherein the chamber 406 comprises a control apparatus including a computing device capable of processing data; microprocessors, programmable logic arrays, data storage, input devices, output device, human machine interface (HMI) 307 and programmable logic control (PLC). The control apparatus is configured and programmed to position the holder 301 mounted with discharging end 51 and the meter 200 to discharge the fluid sample from the discharging end 51 to each designated collecting container 70, to engage the test strip 201 to the meter 200, to contact the tip of the test strip 201 with each fluid sample in the collecting container 70 while the sample is sucked up to the meter 200 for analysis, to disengage the spent strip 201 to a waste collector 403 from the meter 200 after analysis, and to return to the original position 404 and submerge the discharging end in a disinfection solution.

Another embodiment as described here is an automatic sampling system for sampling from a bioreactor vessel comprising
  A) A holding assembly secured to the bioreactor vessel through a standard opening port on the head plate or top of the bioreactor vessel; wherein the assembly is to hold a rigid sampling tube and managed to hold a rigid sampling tube steadily to reach inside of the vessel;
  B) a connector connecting the rigid sampling tube and a flexible tubing outside of the vessel, wherein the flexible tubing is further connected with a rigid discharging end in the end;
  C) a positive displacement pump coupled with the flexible tubing to transport the sample fluid from inside of the bioreactor vessel through the sampling tube, flexible tubing and discharging end to a designated sample collecting container;
  D) a tray assembly comprising an array tray configured to hold the at least one sample collecting container;
  E) A positioning assembly coupled with the sampling assembly comprising a X-Y-Z position table or a X-Y position table equipped with a linear actuator and a motor for positioning along the Z-axis wherein the table is coupled with the sampling assembly to position the discharging end of the sampling assembly on the table; and
  F) A control apparatus connected by wire or wirelessly to the sampling assembly and positioning assembly wherein the control apparatus is configured and programmed to coordinate the positioning of the discharging end for delivering the sample fluid to the designated sample collecting container, wherein the apparatus is also configured to control the temperature of a cabinet comprising the sample collecting container, the positioning assembly and the control apparatus.

As disclosed herein an automatic sampling system comprises a sampling assembly, a positioning assembly, a control apparatus and an enclosed cabinet for sampling from a bioreactor vessel not limited to 2, 3, 4, 5, 6, 7, 8, 9, and 10. The collected samples are stored in the cabinet for further analysis using an analytical instrument. Unlike most sampling systems for a bioreactor the disclosed system allows to sample automatically any quantity of sample from a bioreactor aseptically without any waste and any residual sample remaining in the sampling line. The bioreactor can be a device which controls a biologically active environment, or a device for containing and controlling a glucose reaction.

As disclosed herein the sampling assembly comprises a holding assembly wherein the assembly is screwed on a standard opening port commonly the size of 12 mm ID (inner diameter) or the like on the top or head plate of the vessel and configured to hold steadily a rigid sampling tube reaching inside of the vessel to collect the liquid sample. The sample tube is a long rigid tube fixed and secured by a fitting and O-ring on the holding assembly through the center of the assembly. The rigid sampling tube can be held in two ways: (1) the rigid sampling tube held in the holding assembly is fixed and sealed in the assembly and the tip of the sampling tube is always submerged below the liquid level of the bioreactor vessel; (2) the rigid sampling tube held in the holding assembly is movable, wherein the assembly comprises a solid body extended to inside of the bioreactor vessel 100 with a narrow opening in the center to accommodate the rigid movable sampling tube to slide freely and steadily up and down inside of the bioreactor vessel 100. In order to achieve the exact amount of sample being collected aseptically without any waste of sample and any residual remaining in the sampling line, the sampling assembly and sampling procedure will be different for these two methods described above.

For using the fixed sampling tube, a flexible tubing connected to the rigid sampling tube is branched off before the rigid discharging end with another flexible tubing equipped with a check valve followed with an air filter in the end, wherein a pinch valve is applied on the main flexible tubing before the discharging end and another pinch valve is applied on the branched tubing before the air filter.

In FIG. 1 is illustrated a schematic diagram of an automatic sampling system with a fixed rigid sampling tube 31 to sample the fluid sample from a bioreactor or a chemical bioreactor vessel 100. The sampling tube 31 is sealed and fixed on the holding assembly 20 on a head plate 101 of the vessel and is submerged below liquid level 102. After the discharging end 51 is positioned for sampling and discharging to the collecting container 70, the pinch valve 62 is opened, the pump 60 is activated to pump forward, and a given amount of the fluid sample is pumped from the vessel 100 and collected in the container 70. The pump is stopped and the pinch valve 62 is closed and valve 61 which is open to the sterile air filter 63 is opened. The check valve 63 on the tubing prevents the sample fluid from flowing toward the filter 63. The pump 60 is reactivated in the reverse direction and the sample fluid remaining in the tubing 50 is flown back to the vessel 100. Then the pump 60 is stopped and the pinch valve 61 is closed and pinch valve 62 re-opened. The pump 60 is reactivated to pump forward to purge out the small amount of remaining sample fluid between Y-connector 53 and discharging end 51 to the collecting container 70. At this point, there is some sample fluid is pumped up to the tubing 50 again. The pinch valve 61 is re-opened and valve 62 is closed. The pump 60 is reactivated reversely to flush out the last remaining fluid sample back to the vessel 100 and the pinch valve 61 is closed for the next sampling cycle. As noted the pump 60 is bi-directional and the connector 10 is fixed with the rigid sampling tube 31. The entire sampling process is under aseptic condition and there is no waste sample. The entire sampling tubing is clear after sampling and ready for the next sampling. The integrity of the entire process is intact. The advantage of this sampling device and method is simple and requires no moving part of the sampling assembly contacting the sample fluid. But it is required to flush portion of the sampled fluid back to the vessel to clear the line aseptically.

For using the movable rigid sampling tube, the connector connected with the rigid sampling tube in one end is also movable. In the other end the movable connector is connected with the flexible tubing equipped with a check valve and ended with a discharging end; wherein the movable connector is further connected with the holding assembly using a retractable tube; wherein the movable connector is further coupled and driven with a driving assembly, wherein the driving assembly comprises a linear actuator and a motor secured in a fixed position by a supporting frame or holder secured on or around the bioreactor vessel and moves the movable connector along with the sampling tube up and down through the center opening of the holding assembly. As noted the rigid sampling tube is enclosed inside of the retractable tube and form a closed system. As the movable connector is driven downward by a driving assembly, the tube is compressed and the rigid sampling tube moves downward and submerges below the liquid level of the bioreactor vessel. Likewise, as the movable connector is driven upward by the driving assembly, the tube is expanded and the rigid sampling tube moves upward and emerges above the liquid level of the bioreactor vessel.

A linear actuator driven by a motor or the like secured in a fixed position by a supporting frame or a holder on or around the bioreactor vessel and is connected with the movable connector to move up and down along with the rigid sampling tube through the holding assembly to submerge into or emerge from the fluid of the bioreactor vessel; the motor is a linear motor wherein the electric motor that has had its stator and rotor "unrolled" so that instead of producing a torque (rotation) it produces a linear force along its length. If the motor is a regular electric motor, the linear actuator is a mechanical actuator based on simple rotating screw and nut to create the linear motion.

In FIG. 2 is illustrated the schematic diagram of an automatic sampling system with a movable rigid sampling tube to sample the fluid sample from the bioreactor vessel 100 in the following steps (A) the linear actuator 40 secured by a fixed support frame 80 on the head plate 101 of the bioreactor 100 pushes the movable connector 10 along with the sampling tube 31 downward and submerges below the liquid level 102 for sampling. The pump 60 is then activated for a given time to draw a given amount of fluid sample from the vessel 100. And then the pump is stopped and (B) the linear actuator 40 is activated and retracts the movable connector 10 along with the sampling tube 31 upward and off the liquid level 102, then the pump 60 is reactivated and continues to pump the entire remaining fluid sample in the sampling tube 31, flexible tubing 50 and discharging end 51 to the collecting container 70.

By following this sampling procedure the exact quantity of sampled fluid can be taken and always moved forward and never backward. The rigid sampling tube is withdrawn from the liquid the bioreactor vessel 100 and allowed the pump to continue to clear the residual without any waste.

In FIG. 3 is further illustrated the detail parts of the sampling assembly 1 with a movable rigid sampling tube including (A) movable connector 10, (B) holding assembly 20, (C) retractable tube 30 and sampling tube 31, (D) linear actuator 40 and motor 41, (E) flexible tubing 50 and discharging end 51 and (F) positive displacement pump 60. The holding assembly 20 with O-rings 21 is inserted into the standard opening port and secured by the open screw cap 22. A linear actuator 40 is connected with the movable connector 10 and driven by the linear actuator 40 and motor 41 to move it up and down through the center 24 of the assembly 20. The bottom opening of the movable connector 10 with the luer lock 11 is connected with the rigid sampling tube 31 which can be needle, tube or pipe depending on the sample size and the other opening in the side with luer lock 12 is connected with a flexible tubing 50 equipped with a check valve 52 and a rigid discharging end 51 at the end which can be needle, tube or pipe depending on the sample size; The check valve 52 prevents the fluid inside of the tubing from flowing back to the bioreactor vessel 100. A retractable tube 30 is used to connect one lower end 13 of the connector 10 and another end of the holding assembly 23.

As disclosed herein the sampling assembly wherein the integrated part of the assembly which contacts the sample fluid including sampling tube, movable connector, retractable tube, flexible tubing and discharging end is made of single use materials such as plastic which cannot stand autoclave but only gamma irradiation or ethylene oxide sterilization, or is made of autoclavable reusable materials such as stainless steel, glass, polycarbonate, polypropylene, PTFE resin and polymethylpentene. The sampling assembly can therefore be used in a single use bioreactor as an integrated single use system.

As disclosed herein the sampling assembly comprises a positive displacement pump with a channel but not limited to 2, 3, 4, 5, 6, 7 and 8 wherein each channel of the pump is coupled with the flexible tubing of a bioreactor to transport the fluid sample from inside of the bioreactor through the tubing and the discharging end to each designated collecting container; the positive displacement pump preferably is a peristaltic pump or the like to transport fluids without exposing those fluids to contamination from exposed pump components. The pump is intended to move the fluid inside of the flexible tubing forward only in one direction.

As disclosed herein the sampling assembly comprises a holding assembly wherein the holding assembly is secured by an open screw cap on each of the bioreactor vessel through one of its standard open ports on the side or bottom of the vessel and sealed with a O-ring; and a movable connector wherein the movable connector comprises two separate paths, of which one end of the first path is connected with the rigid sampling tube and another end is connected with the flexible tubing with a rigid discharging end at the end; and one end of the second path is connected with an air inlet control valve wherein the valve is connected to a sterile air supply and another end is open to the chamber enclosed inside of the retractable tubing. The sterile air is supplied during the sampling process to maintain a positive pressure and form an air lock inside of the chamber of the sampling assembly to block the fluid getting inside of the chamber. As a result when the sampling tube is retracted back inside of the holding assembly the sampling tube is apart from the fluid inside of the bioreactor and allowed the remaining fluid inside of the sampling tube and flexible tubing continuing to be delivered entirely to the collecting container.

In FIG. 4 is shown the movable connector 10A of the sampling assembly used for sampling the sample fluid from the side or bottom of vessel 100 as shown in FIG. 5, wherein the connector comprises the connecting opening 11A and 12A for the rigid sampling tube and flexible tubing respectively and another opening 14A for connecting to the sterile air supply and the opening 15A is open to the chamber 33A enclosed by the retractable tube 30A as shown in FIG. 5.

In FIG. 5 is illustrated the schematic diagram of the sampling assembly on a bioreactor 100 as (A) the linear actuator 40A secured by a fixed support frame or holder 80A on the side of the bioreactor vessel 100 moves the movable connector 10A along with the sampling tube 31A forward and submerges into the fluid of vessel 100 for sampling. In the same time the sterile air supply 110A enters the chamber 33A and forms the airlock inside the chamber 33A. The peristaltic pump is activated for a given time and a given amount of fluid sample is withdrawn from the vessel 100. And then the pump is stopped and (B) the linear actuator 40A is activated and moves the movable connector 10A along with the sampling tube 31A backward and retracts into the holding assembly 20A and blocked out the fluid of vessel 100, then the pump is reactivated and continues to pump the entire remaining fluid sample in the sampling tube 31A, flexible tubing 50A and discharging end 51A to the collecting container 70A.

As disclosed herein an array tray configured to hold the at least one sample collecting container wherein the array tray is a tray comprising organizing array to hold each sampling collecting container in designated position and allow the control apparatus to direct the discharging end to discharge and store the sample at the designated position.

As disclosed herein a positioning assembly comprises a X-Y-Z position table or a X-Y position table with a linear actuator and motor wherein the position X-Y-Z table provides horizontal and vertical motions for automated machinery such as assembly robots in manufacturing facilities. The table is also known as X-Y-Z stages and is motorized linear slides with linear motion based in bearings which are driven by three drive mechanisms, typically three linear motors or the like; Alternatively the position X-Y table provides horizontal motion for automated machinery such as assembly robots in manufacturing facilities. The table is also known as X-Y stages and is motorized linear slides with linear motion based in bearings which are driven by a drive mechanism, typically two linear motors or the like. The X-Y table is mounted vertically with a linear actuator with a linear motor on one horizontal slide to perform the vertical motion along Z-direction.

As disclosed herein a positioning assembly further comprises a discharging end wherein the discharging end is secured at the X-Y-Z table or the like of the positioning assembly to be positioned to discharge the fluid sample from the bioreactor to the designated collecting container.

As disclosed herein a control apparatus is connected wired or wirelessly with the sampling assembly and positioning assembly wherein the control apparatus is configured and programmed to coordinate the positioning of the sampling tube by the linear actuator and motor of the sampling assembly to the vessel fluid for sampling, the activation of the positive replacement pump to pump the sample through the flexible tubing, the positioning of discharging end on the X-Y-Z table or the like for delivering the fluid sample to a designated collecting container. The apparatus is also configured to control the temperature of the cabinet where the fluid samples are located. The control apparatus may include one or more computing devices capable of processing data; microprocessors, programmable logic arrays, data storage, input devices, output device; human machine interface (HMI) and programmable logic control (PLC) etc.

As disclosed herein an enclosed cabinet comprises a chamber wherein the chamber comprises a discharging end and collecting container of the sampling assembly and the X-Y-Z position table or the like and the temperature of the chamber is controlled; and another chamber wherein the chamber comprises a control apparatus. The chamber is enclosed and controlled at a constant temperature by a heating and cooling mechanism with a temperature controller for the best temperature condition for storing the samples for further processing. The heating mechanism can be hot air or water or the like and cooling mechanism can be superconductive refrigeration or cooling water or the like.

As disclosed herein the automatic sampling system for sampling the fluid of a bioreactor vessel, wherein the bioreactor vessel is a bioreactor vessel for microbial or cell cultures which requires operating under sterile condition or a bioreactor vessel for chemical reaction which requires operating under non-sterile condition. All components of the automatic sampling system which contact the sample fluid is sterilizable and remains integrity with the bioreactor during the entire culturing process. The rigid sampling tube can also be a needle and the sample collecting container can be a sterile bottle or vial with septum.

The positioning assembly, control apparatus and enclosed cabinet are identical to those of the automatic sampling and glucose monitoring system aforementioned as shown in FIG. 7-9 except deleting the glucose monitoring assembly including a meter and a tray of test strip.

Another embodiment as described here is an automatic glucose measurement system for analyzing the glucose concentration of the fluid samples in a collecting container comprising A) A glucose measurement assembly comprising a handheld blood glucose meter coupled with a test strip for analyzing and displaying the glucose concentration of the sample fluid;

B) A tray assembly comprising an array tray configured to hold a sample collecting container and a test strip of the glucose monitoring assembly;

C) A positioning assembly coupled with the glucose measurement assembly comprising a X-Y-Z position table or a X-Y position table equipped with a linear actuator and a motor for positioning in the Z-axis wherein the table is coupled with the glucose measurement assembly to position the meter of the glucose measurement assembly on the table; and D) A control apparatus connected by wire or wirelessly to the glucose measurement assembly and positioning assembly wherein the control apparatus is configured and programmed to coordinate the positioning of the meter to engage it with a designated test strip, then to contact the test tip to the sample fluid of the designated sample collecting container and further suck up the sample fluid by capillary action to the meter for analysis and finally disengage the strip from the meter to the waste collector, wherein the apparatus is also configured to control the temperature of a cabinet comprising the sample collecting container, the glucose measurement assembly, the positioning assembly and the control apparatus.

As disclosed herein a glucose measurement assembly comprises a handheld glucose meter wherein the meter is used to analyzing and displaying the glucose concentration of culture fluid; and a testing strip wherein the enzyme is impregnated on the strip for analyzing the glucose conversion rate of the sample fluid from which the glucose concentration is determined. The handheld glucose meter is the most popularly used blood glucose meter for measurement blood glucose concentration for diabetes. It is simple, fast and very inexpensive. If the meter is recalibrated with the culture medium, the glucose concentration of cell culture medium can be theoretically determined. Currently most of glucose measurement for bioprocessing in market is using the same electrochemical method. Further development using the same electrochemical and optical technologies has progressed to include more than 10 glucoses in one sample such as pH, pCO2, PO2, Na+, K+, Cl−., Ca++, Gluc and Lac. Nova Bioprofile is one of the examples. However the instrument is expensive and not very affordable. The control of glucose concentration is often the most useful control strategy in the bioprocess control of cell culture. There is no affordable on-line or off-line glucose measurement instrument available in the market for microbial or cell cultures. In this innovation the automation of using this very inexpensive and simple handheld glucose meter along with on-line calibration of culture standard medium makes this application feasible. The handheld glucose meter is equipped with RS282 or RS485 serial communication system to transmit the glucose measurement data to the central computer for storage and/or processing.

As shown in FIG. 6 the glucose measurement assembly comprising a commercial handheld blood glucose meter 200 and a test strip 201 is identical to that of the automatic sampling and glucose monitoring system aforementioned except deleting the rigid discharging end.

As disclosed herein a positioning assembly comprises a X-Y-Z position table or a X-Y position table with a linear actuator and motor wherein the position X-Y-Z table provides horizontal and vertical motions for automated machinery such as assembly robots in manufacturing facilities. The table is also known as X-Y-Z stages and is motorized linear slides with linear motion based in bearings which are driven by three drive mechanisms, typically three linear motors or the like; Alternatively the position X-Y table provides horizontal motion for automated machinery such as assembly robots in manufacturing facilities. The table is also known as X-Y stages and is motorized linear slides with linear motion based in bearings which are driven by a drive mechanism, typically two linear motors or the like. The X-Y table is mounted vertically with a linear actuator with a linear motor on one horizontal slide to perform the vertical motion along the Z-direction.

As disclosed herein a positioning assembly comprises a discharging end wherein the discharging end is secured at the X-Y-Z table or the like of the positioning assembly to be positioned to discharge the fluid sample from the bioreactor to the designated collecting container.

As disclosed herein a the control apparatus is connected wired or wirelessly with the sampling assembly and positioning assembly wherein the control apparatus is configured and programmed to coordinate the positioning of the sampling tube by the linear actuator and motor of the sampling assembly to the vessel fluid for sampling, the activation of the positive replacement pump to pump the sample through the flexible tubing, the positioning of discharging end on the X-Y-Z table or the like for delivering the fluid sample to a designated collecting container. The apparatus is also configured to control the temperature of the cabinet where the fluid samples are located. The control apparatus may include one or more computing devices capable of processing data; microprocessors, programmable logic arrays, data storage, input devices, output device; human machine interface (HMI) and programmable logic control (PLC) etc.

As disclosed herein an enclosed cabinet comprises a chamber wherein the chamber comprises a discharging end and collecting container of the sampling assembly and the X-Y-Z position table or the like and the temperature of the chamber is controlled; and another chamber wherein the chamber comprises a control apparatus. The chamber is enclosed and controlled at a constant temperature by a heating and cooling mechanism with a temperature controller for the best temperature condition for storing the samples for further processing. The heating mechanism can be hot air or water or the like and cooling mechanism can be superconductive refrigeration or cooling water or the like.

The positioning assembly, control apparatus and enclosed cabinet are identical to those of the automatic sampling and glucose measurement system aforementioned as shown in FIG. 7-9 except deleting the rigid discharging end of the sampling assembly.

What is claimed is:

1. An automated bioreactor sampling and glucose monitoring system comprising:
   a bioreactor containing culture fluid and in fluid connection with
   a sampling assembly comprising:
      a holding assembly secured on an open port of the bioreactor to hold a rigid sampling tube to deliver a sample from the bioreactor;
      a connector connecting the rigid sampling tube and a flexible tubing constructed and arranged outside of the bioreactor, wherein the flexible tubing has a discharging end;
      a positive displacement pump operative connected with the flexible tubing to transport a sample fluid from inside of the bioreactor through the sampling tube, flexible tubing and discharging end to a sample collecting container;
   a glucose monitoring assembly in fluid connection with the sampling assembly wherein the sampling assembly is in operative connection to a handheld glucose meter to analyze and record the glucose concentration of the sample fluid and a tray assembly comprising an array tray to hold at least one sample collecting container and a test strip in operative connection with the handheld glucose meter;
   a positioning assembly in operative connection with the sampling assembly and the glucose monitoring assembly wherein the position assembly comprises an X-Y-Z positioning table or a X-Y positioning table equipped with a linear actuator and a motor for position the tray assembly along the Z-axis; and a wire or wireless controller in operative connection to the sampling assembly, glucose monitoring assembly and positioning assembly, wherein the controller controls positioning of the rigid sampling tube and the positive displacement pump to take sample fluid from the bioreactor, positioning of the sample fluid at the discharging end to deliver the sample fluid to a collecting container on the array tray table, positioning of glucose meter of the glucose monitoring assembly and the test strip in the assay tray for the glucose analysis and controls the temperature of a cabinet wherein the cabinet comprises the discharging end, the array tray, the glucose monitoring assembly, the positioning assembly and the controller.

2. An automated bioreactor sampling and glucose monitoring system of claim 1, wherein the rigid sampling tube held in the holding assembly is fixed and sealingly secured in the assembly and the tip of the sampling tube is always submerged in the culture fluid of the bioreactor.

3. An automated bioreactor sampling and glucose monitoring system of claim 2, wherein the connector is connected with the rigid sampling tube in one end and the flexible tubing in the other end, wherein the flexible tubing is branched into two other ends, the first one is connected to the rigid discharging end and the second one is ended with an air filter, wherein a pinch valve is applied on each branched tubing before the end, wherein an optional check valve is added before the air filter.

4. An automated bioreactor sampling and glucose monitoring system of claim 3, wherein the positive displacement pump is bi-directional.

5. An automated bioreactor sampling and glucose monitoring system of claim 1, wherein the rigid sampling tube connecting the connector is a moving element and not fixed on the holding assembly, wherein the holding assembly comprises a solid body extended to inside of the bioreactor with a narrow opening in the center to accommodate the movable rigid sampling tube to move up and down through the narrow central opening of the holding assembly.

6. An automated bioreactor sampling and glucose monitoring system of claim 5, wherein the connector is connected with the movable rigid sampling tube in one end and in operative connection with a flexible tubing to the discharging end in the other end, wherein the connector is also in operative connection with a retractable tube to the holding assembly, wherein the connector is a moving element and in operative connection with a driving assembly, wherein the driving assembly comprises a linear actuator and a motor secured in a fixed position by a supporting frame or holder secured on the bioreactor to drive and move the movable connector connected with the rigid sampling tube up and down through the central opening of the holding assembly secured on the top of the bioreactor.

7. An automated bioreactor sampling and glucose monitoring system of claim 5, wherein the holding assembly is secured on an open port on the side or bottom of the bioreactor, wherein the movable connector comprises two separate paths, one end of the first path is in operative connection with the rigid sampling tube and another end is in operative connection with the flexible tubing and the rigid discharging end; and one end of the second path is in operative connection with an air inlet control valve wherein the valve is connected to a sterile air supply and another end of the path is open to the chamber enclosed inside of the retractable tubing.

8. An automated bioreactor sampling system comprising:
a bioreactor containing culture fluid and in fluid connection with
a sampling assembly comprising:
a holding assembly secured on an open port of the bioreactor to hold a rigid sampling tube to deliver a sample from the bioreactor;
a connector connecting the rigid sampling tube and a flexible tubing constructed and arranged outside of the bioreactor, wherein the flexible tubing has a discharging end;
a positive displacement pump operative connected with the flexible tubing to transport a sample fluid from inside of the bioreactor through the sampling tube, flexible tubing and discharging end to a sample collecting container;
a positioning assembly in operative connection with the sampling assembly wherein the position assembly comprises an X-Y-Z positioning table or a X-Y positioning table equipped with a linear actuator and a motor for position the tray assembly along the Z-axis; and
a wire or wireless controller in operative connection to the sampling assembly and positioning assembly, wherein the controller controls positioning of the rigid sampling tube and the positive displacement pump to take sample fluid from the bioreactor, positioning of the sample fluid at the discharging end to deliver the sample fluid to a collecting container on the array tray table and controls the temperature of a cabinet wherein the cabinet comprises the discharging end, the array tray, the positioning assembly and the controller.

9. An automated bioreactor sampling system of claim 8, wherein the rigid sampling tube held in the holding assembly is fixed and sealed in the assembly and the tip of the sampling tube is submerged in the culture fluid of the bioreactor.

10. An automated bioreactor sampling of claim 9, wherein the connector is connected with the rigid sampling tube in one end and the flexible tubing in the other end, wherein the flexible tubing is branched into two other ends, the first one is connected to the rigid discharging end and the second one is ended with an air filter, wherein a pinch valve is applied on each branched tubing before the end, wherein an optional check valve is added before the air filter.

11. An automated bioreactor sampling system of claim 10, wherein the positive displacement pump is bi-directional.

12. An automated bioreactor sampling system of claim 8, wherein the rigid sampling tube connecting the connector is a moving element and not fixed on the holding assembly, wherein the holding assembly comprises a solid body extended to inside of the bioreactor with a narrow opening in the center to accommodate the movable rigid sampling tube to move up and down through the narrow central opening of the holding assembly.

13. An automated bioreactor sampling system of claim 12, wherein the connector is connected with the movable rigid sampling tube in one end and in operative connection with a flexible tubing to the discharging end in the other end, wherein the connector is also in operative connection with a retractable tube to the holding assembly, wherein the connector is a moving element and in operative connection with a driving assembly, wherein the driving assembly comprises a linear actuator and a motor secured in a fixed position by a supporting frame or holder secured on the bioreactor to drive and move the movable connector connected with the rigid sampling tube up and down through the central opening of the holding assembly secured on the top of the bioreactor.

14. An automated bioreactor sampling system of claim 13, wherein the holding assembly is secured on an open port located on the side or bottom of the bioreactor, wherein the movable connector comprises two separate paths, one end of the first path is in operative connection with the rigid sampling tube and another end is in operative connection with the flexible tubing and the rigid discharging end; and one end of the second path is in operative connection with an air inlet control valve wherein the valve is connected to a sterile air supply and another end of the path is open to the chamber enclosed inside of the retractable tubing.

15. An automated glucose measurement system for a sample fluid in a sample collecting container comprising:

a glucose monitoring assembly is in operative connection to a handheld glucose meter and a test trip to analyze and record the glucose concentration of a sample fluid held in a sample collecting container;

a tray assembly comprising an array tray to hold at least one of the sample collecting container and the test strip in operative connection with the handheld glucose meter a positioning assembly is in operative connection with the tray assembly and the glucose monitoring assembly wherein the position assembly comprises an X-Y-Z positioning table or a X-Y positioning table equipped with a linear actuator and a motor for position the tray assembly along the Z-axis; and a wire or wireless controller is in operative connection to the glucose monitoring assembly, tray assembly and positioning assembly, wherein the controller controls positioning of the handheld glucose meter and the test strip for the glucose analysis.

* * * * *